United States Patent [19]

Heuvelsland

[11] Patent Number: 4,764,626

[45] Date of Patent: Aug. 16, 1988

[54] METHOD FOR PRODUCING 1,4-DIOXANE

[75] Inventor: Albert J. Heuvelsland, Heikant, Netherlands

[73] Assignee: The Dow Chemical Company, Midland, Mich.

[21] Appl. No.: 722,544

[22] Filed: Apr. 12, 1985

[51] Int. Cl.$^4$ ............................................. C07D 319/12
[52] U.S. Cl. ....................................................... 549/377
[58] Field of Search ........................................... 549/377

[56] References Cited

FOREIGN PATENT DOCUMENTS 2300990 7/1974 Fed. Rep. of Germany .
2430355 6/1976 Fed. Rep. of Germany .

OTHER PUBLICATIONS

Kuboya, Kametani & Inuzuka, "On the Formation of 1,4-Dioxane from Ethylene Glycol or Diethylene Glycol with Benzenesulfinic Acid", (Engl.) (With Japanese publication attached).

Primary Examiner—Nicky Chan

[57] ABSTRACT

A 1,4-dioxane is produced by subjecting a one-phase liquid reaction mixture of at least one compound of the general formula:

$$RO-(CH_2CH_2O)_n-R \qquad (I)$$

where n is an integer from 1 to 6 and each R is individually a hydrogen atom or an alkyl group containing 1 to 5 carbon atoms and a dehydration catalyst to a subatmospheric pressure and an elevated temperature sufficient to prepare 1,4-dioxane, which is removed as an overhead product. The method substantially reduces foaming and formation of tars and increases productivity.

9 Claims, No Drawings

METHOD FOR PRODUCING 1,4-DIOXANE

BACKGROUND OF THE INVENTION

The present invention relates to a continuous method for producing 1,4-dioxane.

There are a variety of methods known for the continuous preparation of 1,4-dioxane. The most widely employed commercial methods for the continuous preparation of 1,4-dioxane consists of dehydrating ethylene glycol, a polyethylene glycol, a mixture of ethylene glycol and one or more polyethylene glycol(s) or a mixture of polyethylene glycols in the presence of a sulfuric acid catalyst. The dehydration reaction is conducted at an elevated temperature, usually above 170° C. and at atmospheric pressure. The reaction product which consists of 1-4 dioxane, water and by-products is continuously removed from the reaction mixture as an overhead product, condensed and the 1,4-dioxane subsequently separated from the water and by-products. As the 1,4-dioxane is removed from the reactor and the sulfuric acid is deactivated, additional amounts of the glycol(s) and sulfuric acid are added to the reactor. Unfortunately, severe charring and the formation of tars are inherent in the sulfuric acid catalyzed method for preparing 1,4-dioxane, which results in losses in product yield. In addition, foaming in the reactor causes the tars to be carried over into the product, thereby causing discoloration of the reaction product. The formation of tar and its subsequent carry-over into the product require the vessels and equipment used in the process to be cleaned on a frequent basis.

In an alternative method for producing 1,4-dioxane, German Offenlegungschriften Nos. 2,430,355 and 2,300,990 describe dehydrating polyethylene glycol to 1,4-dioxane using a solid cation exchange resin as the dehydration catalyst. The reaction is conducted at an elevated temperature below 170° C. and a sub-atmospheric pressure to increase the rate of dioxane distillation. Unfortunately, the ion exchange resins are inherently unstable at the reaction temperatures employed. In addition, the handling difficulties associated with a solid/liquid reaction system lead to increased operating costs and capital investment.

U.S. Pat. No. 3,825,568 discloses yet another method for the production of 1,4-dioxane. In the described method, ethylene oxide is dimerized in the presence of SiF$_4$ or BF$_3$ or the adduct formed from BF$_3$ and 1,4-dioxane in the liquid phase at temperatures from −50° C. to 0° C. and at an atmospheric pressure or a pressure greater than atmospheric pressure. Due to their corrosive and other undesirable properties, compounds such as BF$_3$ and SiF$_4$ require special handling.

In view of the stated deficiencies, it would be advantageous to develop a process for the preparation of 1,4-dioxane which does not exhibit the deficiencies of the prior art processes.

SUMMARY OF THE INVENTION

Accordingly, the present invention is a method for the continuous preparation of 1,4-dioxane which does not exhibit the deficiencies of the described prior art processes. The method comprises subjecting a one phase liquid reaction media comprised of (1) one or more compounds of the general structural formula:

$$RO-(CH_2CH_2O)_n-R \qquad (I)$$

wherein each R is individually hydrogen or an alkyl group of from 1 to 5 carbon atoms and n is an integer between 1 and 6 and (2) a dehydration catalyst to a pressure and at an elevated temperature sufficient to prepare 1,4-dioxane, continously removing the 1,4-dioxane reaction product from the reactor and adding more of the compound of formula (I) to the reactor, characterized by the fact that the reactor pressure is subatmospheric.

Surprisingly, it has been found that simply allowing the reaction to take place at subatmospheric pressures eliminates the deficiencies of the commercial catalytic dehydration process operated at atmospheric pressures. Specifically, the formation of tars is unexpectedly and significantly reduced. In addition, in contrast to what was expected, the foaming of the reaction mixture is reduced. Therefore, the discoloration of the reaction product by carry-over of tar from the reaction vessel is eliminated. Moreover, using a subatmospheric reaction pressure, the catalytic activity of the dehydration catalyst is increased. Although the reactor still must be cleaned periodically due to deposits of tars and charring, the period between such shut downs for cleaning are increased by as much as two to three times using the method of the present invention as compared to an identical process except employing atmospheric reactor pressure (i.e., 760 mm Hg).

DETAILED DESCRIPTION OF THE INVENTION

In the method of the present invention, the preferred reactants are ethylene glycol (each R is hydrogen and n is 1 in formula (I)) and polyethylene glycol (each R is hydrogen and n is 2 to 6). More preferably, the reactant is diethylene glycol, triethylene glycol or a mixture of said glycols. Diethylene glycol is the most preferred reactant.

Suitable materials useful as dehydration catalysts are those materials capable of catalyzing the dehydration reaction and forming a single phase with the reactant(s), i.e., the catalyst is soluble in or miscible with the reactant(s). Representative of such materials are p-toluene sulfonic acid, phosphoric acid and sulfuric acid. Preferably, the dehydration catalyst is sulfuric acid.

The amounts of the reactant and catalyst most advantageously employed are dependent on various factors including the specific reactant and catalyst employed and the conditions of the reaction, particularly its temperature. Specifically, the rate of reaction is proportional to the amounts of acid catalyst employed and the catalyst level selected accordingly. The minimum catalyst concentration is dependent on the minimum desired rate of reaction whereas the maximum concentration is limited by the amounts of the reaction product capable of being handled (e.g., condensed by the overhead condensor) as well as practical limitations. In general, the catalyst is advantageously employed in an amount from 0.2 to 30 weight percent based on the total weight of the reactants employed. Preferably, the catalyst is employed in an amount from 1 to 14, more preferably from 3 to 10, weight percent based on the total weight of the reactant(s).

In the method of the present invention, the reactant and the dehydration catalyst are admixed and the dehydration reaction conducted using continuous techniques. Such techniques comprise continuously adding the desired amounts of the reactant(s) and dehydration catalyst to a reactor maintained at conditions sufficient to dehydrate the reactant(s). The 1,4-dioxane product, as well as the water formed by the reaction and by-products, are subsequently removed from the top of the reactor. New amounts of the reactant(s) and catalyst are added to the reactor to maintain the liquid level in the reactor and to keep the amounts of active dehydration catalyst at a desired level.

In the practice of this invention, the dehydration reaction is conducted at a subatmospheric pressure and an elevated temperature. The specific pressure and temperature most advantageously employed depends on a variety of factors including the specific reactant(s) and dehydration catalyst employed and the desired rate of reaction. In general, the rate of reaction increases as the reactor pressure decreases, and, for maximum yields, the reactor pressure is maintained as low as practical. However, the reactor pressure must be sufficient to prevent the flashing of the reactant(s). In general, the reactor is advantageously maintained at a pressure from 10 to 750 millimeters of mercury (mm Hg). Preferably, the reactor pressure is maintained, during the reaction, at a pressure from 15 to 600, more preferably from 25 to 550, mm Hg. Such reduced pressure is easily obtained using a vacuum pump or other suitable evacuation means. In general, the reaction is preferably conducted at a temperature from 140° to 190° C., more preferably from 145° to 180° C. Most preferably, the reaction is conducted at a temperature from 150° to 170° C. and a pressure from 50 to 400 mm Hg.

The reactant(s) and dehydration catalyst are maintained at the specified temperature and pressure for a sufficient residence time to allow the desired conversion of the reactant to 1,4-dioxane while minimizing, to the most practical extent, the occurance of side reactions and/or formation of by-products. In general, an average residence time of from 0.5 to 20 hours at the specified reaction conditions, is preferred.

The 1,4-dioxane reaction product, with the water formed during the desired dehydration reaction and reaction by-products such as acetaldehyde and 2-methyl-1,3-dioxolane is removed from the reactor overhead as a volatile and subsequently condensed. The 1,4-dioxane can subsequently be recovered free of water and at any desired purity from the product removed from the reactor using further distillation and/or other well-known separation techniques.

The following examples are presented to illustrate the method of the present invention and should not be construed to limit its scope. In the examples, all parts and percentages are by weight unless otherwise indicated.

EXAMPLE 1

A single phase liquid mixture of 100 parts diethylene glycol and 3.2 parts sulfuric acid was added to a one liter glass flask equipped with a stirrer, an electric heating element, a thermometer, an overhead condenser and a vacuum pump. The mixture in the glass flask was heated slowly to 143° C. while the pressure in the flask was maintained at 400 mm Hg. A distillate containing 1,4-dioxane, water and by-products were continuously obtained as an overhead product and condensed. Diethylene glycol was added continuously to maintain the liquid level in the flask as the reaction product is removed as an overhead from the reactor. The overhead product, during steady-state operation, was collected and analyzed for its composition. It contained 20 percent water with the remainder being as specified in Table I.

EXAMPLE 2

The procedure of Example 1 was duplicated except that the temperature of the reaction was maintained at 152° C. The overhead product during steady state operation, was collected and analyzed for its composition. It contained 20 percent water with the remainder as being specified in Table I.

EXAMPLE 3

The procedure of Example 2 was repeated except that the temperature of the reaction was maintained at 160° C. An analysis (dry basis) of the overhead product, collected during steady state operation, is set forth in Table I.

TABLE I

| Example No. | 1 | 2 | 3 |
|---|---|---|---|
| Product Composition, wgt % (dry basis) | | | |
| 1,4-dioxane | 96.9 | 96.0 | 94.6 |
| Acetaldehyde | 1.87 | 2.35 | 3.07 |
| 2-Methyl-1,3-dioxolane | 1.1 | 1.65 | 2.25 |
| Crotonaldehyde | 0.04 | 0.06 | 0.12 |
| Ethanol | 0.02 | 0.03 | 0.04 |

As evidenced by the data in Table I, 1,4-dioxane of high purity (on a dry basis) is prepared by the method of the present invention. The selectivity of the reaction to 1,4-dioxane was found to be higher at lower reaction temperatures. Of primary importance was the fact that the reactions carried out in Examples 1–3 were characterized by the absence of tar formation and excessive foaming in the reaction flask.

COMPARATIVE EXAMPLE A

The method of Example 1 was repeated except that the reactor pressure was maintained at atmospheric pressure (about 760 mm Hg). During the reaction, excessive foaming and tar formation was evidenced. The overhead product prepared by the reaction contained 95 percent 1,4-dioxane. (on a dry basis).

EXAMPLE 4

The method of Example 1 was repeated except that a mixture of 100 parts of diethylene glycol and 0.7 part of sulfuric acid were contacted at a temperature of 170° C. and at a pressure of 400 mm Hg.

EXAMPLE 5

The procedure of Example 4 was repeated except that a reaction temperature of 184° C. was employed.

EXAMPLE 6

The procedure of Example 4 was repeated except that a reaction temperature of 187° C. was employed.

The overhead product from each of Examples 4–6 were obtained during steady state operation. The composition of each sample was analyzed and the results of the analyses (on a dry basis) are set forth in Table II.

TABLE II

| Example No. | 4 | 5 | 6 |
|---|---|---|---|
| Product | | | |

TABLE II-continued

| Example No. | 4 | 5 | 6 |
|---|---|---|---|
| Composition, wgt % (dry basis) | | | |
| 1,4-dioxane | 94.2 | 92.6 | 93.0 |
| Acetaldehyde | 3.7 | 3.7 | 3.8 |
| 2-Methyl-1,3-dioxolane | 1.72 | 3.6 | 3.0 |
| Crotonaldehyde | 0.09 | 0.09 | 0.12 |
| Ethanol | 0.04 | 0.04 | 0.05 |

Again, the reaction conducted in Example 4–6 was characterized by the absence of tar formation and excessive foaming in the flask.

COMPARATIVE EXAMPLE B

The method of Example 4 was repeated except that the reactor pressure was maintained at atmospheric pressure (about 760 mm Hg). During the reaction, excessive foaming and tar formation was evidenced.

EXAMPLE 7

The method of Example 1 was repeated except that the concentration of the sulfuric acid was maintained at 4.5 percent based on the weight of the diethylene glycol and the reaction was conducted at 146° C. and a pressure of 547 mm Hg. The productivity of the reaction, measured as the amount of reaction product (including water) produced per cubic meter of reactor volume per hour, was measured at steady state operation and is set forth in Table III.

EXAMPLES 8–12

A series of experiments were conducted using the method of Example 7 except that the reactor pressure was maintained at the pressure specified in Table III. The productivity for the reaction at each pressure was measured and is also set forth in Table III.

COMPARATIVE EXAMPLE C

A test run was conducted using the method of Example 7 except that the reactor pressure was maintained at atmospheric pressure (i.e., 760 mm Hg). The productivity of this test run is measured and also set forth in Table III.

TABLE III

| Example No. | 7 | 8 | 9 | 10 | 11 | Comparative Example C |
|---|---|---|---|---|---|---|
| Reactor Pressure, (mm Hg) | 547 | 479 | 304 | 129 | 15 | 760 |
| Productivity kg/m³/hr | 115 | 150 | 176 | 203 | 238 | 84 |

As evidenced by the data in Table III, due to the increased catalyst efficiency, the productivity of the reaction increased as the reactor pressure decreased. Moreover, although Examples 7–12 exhibited no tar formation or excessive foaming, noticable tar formation and foaming was noted during reaction at conditions of Comparative Example C.

EXAMPLE 13

A large scale production operation for converting diethylene glycol to 1,4-dioxane using the method of the present invention was conducted in a production unit consisting of a 1500 liter reaction vessel, a vacuum pump, a condenser means for condensing the overhead product and a temperature control means. The reaction was conducted at a pressure of 300 mm Hg, a temperature of 150° C. and a sulfuric acid concentration of 5 percent by weight based on the weight of diethylene glycol. The diethylene glycol was fed to the reactor at a rate of 500 kg/hr which maintained the level in the reactor. Fresh sulfuric acid was also fed to the reactor at a rate to maintain the five percent concentration level. The reactor was operated continuously for a six week period. The results of the run are shown in Table V.

TABLE V

| Reaction Pressure mm Hg | 300 |
|---|---|
| Reaction Temperature °C. | 150 |
| Feed rate of diethylene glycol kg/hr | 500 |
| Product Composition, % | |
| 1,4-dioxane | 95.5 |
| Acetaldehyde | 2.1 |
| 2-methyl, 1,3-dioxolane | 2.4 |
| Productivity kg/m³/hr | 311 |

During the six week period of operation, the productivity remained consistently high, the formation of tar was negligible and foaming was absent.

What is claimed is:

1. A method for continuously producing 1,4-dioxane which comprises subjecting a one-phase liquid reaction mixture of at least one glycol compound of the general formula:

$$RO-(CH_2CH_2O)_n-R \qquad (I)$$

where n is an integer from 1 to 6 and each R is individually a hydrogen atom or an alkyl group containing 1 to 5 carbon atoms and a dehydration catalyst selected from the group consisting of p-toluene sulfonic acid, phosphoric acid and sulfuric acid and which is miscible with the glycol compound to a subatmospheric pressure and an elevated temperature sufficient to prepare 1,4-dioxane, which is removed as an overhead product, provided that said method substantially reduces foaming and the formation of tars compared to an otherwise identical process conducted at a pressure of 760 mm Hg, thereby substantially increasing productivity and eliminating the discoloration of the 1,4-dioxane product.

2. The method of claim 1 wherein the compound of formula (I) is ethylene glycol, diethylene glycol, triethylene glycol or a mixture thereof.

3. The method of claim 2 wherein the compound of formula I is diethylene glycol.

4. The method of claim 2 wherein the dehydration catalyst concentration is from 1 to 14 percent by weight based on the weight of the glycol compound used, and the reaction temperature is from 140° C. to 190° C.

5. The method of claim 1 wherein the dehydration catalyst is sulfuric acid.

6. The method of claim 1 wherein the reaction pressure is from 15 to 600 mm Hg.

7. The method of claim 6 wherein the reaction pressure is from 25 to 550 mm Hg.

8. A method for continuously producing 1,4-dioxane which comprises subjecting a one phase liquid reaction mixture of sulfuric acid and at least one glycol compound selected from the group consisting of ethylene glycol, diethylene glycol and triethylene glycol to a pressure from 50 to 400 mm Hg and a temperature from 150° C. to 170° C. sufficient to prepare 1,4-dioxane, which is removed as an overhead product, and wherein the sulfuric acid concentration is from 3 to 9 percent by weight based on the weight of the glycol compound used, and which substantially reduces foaming and formation of tars and increases productivity compared to an otherwise identical process conducted at a pressure of 760 mm Hg.

9. A method for continuously producing 1,4-dioxane which comprises subjecting a one-phase liquid reaction mixture of at least one compound of the general formula:

$$RO\text{---}(CH_2CH_2O)_n\text{---}R \qquad (I)$$

where n is an integer from 1 to 6 and each R is individually a hydrogen atom or an alkyl group containing 1 to 5 carbon atoms and a dehydration catalyst to a subatmospheric pressure and an elevated temperature sufficient to prepare 1,4-dioxane, which is removed as an overhead product, provided that said method substantially increases productivity compared to an otherwise identical process conducted at a pressure of 760 mm Hg wherein the reaction temperature is from 150° C. to 170° C., and the dehydration catalyst is sulfuric acid and is present in a concentration from 3 to 9 percent by weight, and the reactor pressure is from 50 to 400 mm Hg.

* * * * *